United States Patent [19]

Peeters et al.

[11] Patent Number: 4,558,126

[45] Date of Patent: Dec. 10, 1985

[54] METHOD OF PREPARING URACIL

[75] Inventors: Hermann Peeters, Niederkassel; Wilhelm Vogt, Cologne, both of Fed. Rep. of Germany

[73] Assignee: Dynamit Nobel AG, Troisdorf, Fed. Rep. of Germany

[21] Appl. No.: 672,342

[22] Filed: Nov. 16, 1984

[30] Foreign Application Priority Data

Nov. 24, 1983 [DE] Fed. Rep. of Germany ....... 3342419

[51] Int. Cl.$^4$ ........................................... C07D 239/54
[52] U.S. Cl. ..................................................... 544/309
[58] Field of Search ........................................ 544/309

[56] References Cited

U.S. PATENT DOCUMENTS

| | | | |
|---|---|---|---|
| 2,417,318 | 3/1947 | Northey | 544/309 |
| 3,718,649 | 2/1973 | Dyer | 544/309 |
| 4,476,306 | 10/1984 | Peeters | 544/309 |

FOREIGN PATENT DOCUMENTS

| | | | |
|---|---|---|---|
| 0746247 | 8/1970 | Belgium | 544/309 |
| 0746245 | 8/1970 | Belgium | 544/309 |
| 0057280 | 8/1982 | European Pat. Off. | 544/309 |
| 54-34671 | 4/1981 | Japan | 544/309 |

*Primary Examiner*—Donald G. Daus
*Assistant Examiner*—Stephen M. Kapner
*Attorney, Agent, or Firm*—Felfe & Lynch

[57] ABSTRACT

A method is disclosed whereby uracil is obtained from alkali formyl acetic acid alkyl esters by reacting such esters with thiourea and then with hydrogen peroxide without isolating the intermediates, and then separating the uracil by precipitation with acids.

10 Claims, No Drawings

METHOD OF PREPARING URACIL

BACKGROUND OF THE INVENTION

The present invention relates to the preparation of 2,4(1H,3H)-pyrimidinedione (uracil) from alkali formyl acetic acid alkyl esters by reaction with thiourea followed by reaction with hydrogen peroxide, without isolation of intermediates, in accordance with the equation:

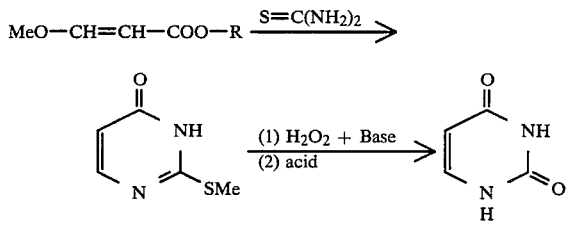

Uracil is a product which has wide application as an industrial chemical, as an agrochemical or as a pharmaceutical starting product (Ind. Chem. Prod. Res. Dev. Vol. 17, No. 4 (1978) 278).

Uracil can be prepared by a number of methods, as described in part in the above-cited literature. The reaction of malic acid with urea in sulfuric acid containing sulfur trioxide has the disadvantage of the need for the disposal or processing or large amounts of dilute organically contaminated sulfuric acid. In the saponification of 2-thiouracil with chloroacetic acid and hydrochloric acid, the formation of mercaptoacetic acid produces an extremely unpleasant odor and the recovery of an odorless uracil is difficult and entails great losses.

The problem existed of preparing uracil in a high yield and purity while avoiding environment-polluting wastes by a method easy to perform on a technical scale, setting out from simple starting materials.

THE INVENTION

It has been possible to solve the problem by reacting alkali formylacetic acid alkyl ester first with thiourea and then with hydrogen peroxide in a "one-pot reaction" at moderate temperatures in an aqueous medium. Surprisingly, the byproducts do not interfere with the reaction and require no isolation of intermediates.

The subject of the invention is a method of preparing uracil

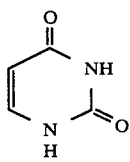   (1)

which is characterized by the fact that an alkali formyl acetic acid alkyl ester <p style="text-align:center;">MeO—CH=CH—COOR     (2)</p> in which Me represents an alkali metal, preferably sodium or potassium and R represents an alkyl moiety of 1 to 8 carbon atoms, preferably a methyl or ethyl moiety, is reacted with thiourea to form the alkali salt of 2-mercapto-4-hydroxypyrimidine

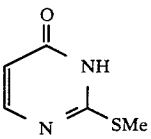   (3)

wherein Me has the same meaning as in Formula 2, and then, without isolation of the substances of Formula 3, the reaction solution is made to react with hydrogen peroxide in aqueous solution, in the presence of at least 2 moles of base per mol of thiourea originally present, and, finally, uracil is formed and recovered by acidification to a pH of 6 or less. The amount of thiourea is 0.95 to 1.05 mol per mol of components (2).

The alkali formyl acetic acid alkyl ester is obtainable by the formylation of acetic acid esters with formic acid esters or carbon monoxide, and can be used in solid or dissolved form, even together with impurities from its preparation.

By the present method, alkali formyl acetic acid alkyl ester is reacted with thiourea first to form the alkali salt of 4-hydroxy-2-mercaptopyrimidine, by the method, for example, of U.S. Pat. No. 3,718,649, and this is further reacted directly with hydrogen peroxide.

For this purpose an alkali formyl acetic acid alkyl ester can be fed, for example, into an aqueous solution of alkali hydroxide and thiourea at temperatures of about 10° to 25° C. and reacted therewith in the temperature range from 20° to 100° C. for about 1 to 2 hours. In the reaction, no free base need be added, but small amounts of free base, from 0.1 mole up, increase the yield. Preferably, 0.5 to 6 moles, and very preferably 2 to 3 moles of base, are added per mole of thiourea.

The concentration of the reaction solution as regards thiourea is to be preferably 0.2 to 6 moles per liter, advantageously 0.5 to 4 moles per liter. The molar ratio of thiourea to alkali formyl acetic ester can be from 0.8 to 1.2:1, preferably 0.9 to 1.1:1.

The reaction product is the alkali salt of 4-hydroxy-2-mercaptopyrimidine, which is easily soluble in water. An aqueous hydrogen peroxide solution is added directly to it. The concentration of the hydrogen peroxide solution is not critical, and can amount, for example to 5 to 85%, by weight, of hydrogen peroxide.

The amount of hydrogen peroxide is to be 2 to 8 moles, preferably 2.5 to 5 moles per mole of thiourea. The reaction with hydrogen peroxide is exothermic. The addition and the reaction are to take place at temperatures from 0° to 150° C., preferably 10° to 100° C.

How long the adding of the hydrogen peroxide solution will take will depend on the concentration of this solution, the addition temperature, and the cooling of the system, and will amount generally to about 5 minutes to 2 hours. Further reaction after addition of components is unnecessary, but can be performed at temperatures of 0° to 150° C., preferably 10° to 100° C., for 5 minutes to 5 hours. The presence of an excess of base is necessary for the achievement of satisfactory yields. The molar ratio of the total base to input thiourea is to amount to 2.5 to 8, preferably 3.5 to 5:1, including the base already added and the base that is present in the form of the alkali formyl acetic acid alkyl ester. The base is preferably alkali hydroxide, especially sodium hydroxide or an aqueous solution thereof, or, if desired, ammonium hydroxide, alkali carbonates, etc. The base can be added either prior to the reaction of the alkali formyl acetic acid alkyl ester with thiourea, or thereafter, or it can be put in together with the hydrogen peroxide.

After the reaction with hydrogen peroxide, the uracil is released by adjusting the reaction mixture with acids, preferably mineral acids or their aqueous solutions, to a pH of less than 6, preferably between 3 and 0.5, whereupon the uracil precipitates out.

Sulfuric acid, hydrochloric acid, nitric acid or phosphoric acid can serve as the mineral acids. The addition of the acid can be performed at temperatures from 0° to 150° C., preferably from 10° to 100° C., within a brief period of time. The after-reaction time amounts to 0 to 2 hours.

Uracil is obtained in a high yield in high purity by filtration and washing with water until it is salt-free, and then drying. The yields obtained can amount to 80% and more, of very pure substance. This appears remarkable in view of the multi-stage synthesis and the easily obtainable starting material.

EXAMPLES

Example 1

73.0 g (0.5 mol) of sodium formyl acetic acid methyl ester (content 85 wt.-%) is added in portions, at 25° C., to a solution of 38 g (0.5 mol) of thiourea and 40 g (1 mole) of sodium hydroxide in 150 ml of water. After 2 hours of reaction at 25° C., 170 g (1.5 moles) of a 30 wt.-% aqueous hydrogen peroxide solution is added over a period of ½ hour, whereupon the temperature increases and is held at 50° C. by cooling. After addition of the hydrogen peroxide, the mixture is cooled to 20° C. and adjusted to pH 1 with concentrated hydrochloric acid. Uracil then precipitates as a colorless solid, which is filtered out, washed with water until salt-free, and dried.

Yield: 44.4 g (79.3% of the theory), melting point 335° C. (decomposition).

Example 2

81.2 g (0.5 mol) of sodium formyl acetic acid ethyl ester (content 85 wt.-%) is reacted and processed as in Example 1.

Yield: 41.7 g (74.5% of the theory).

Example 3

73.0 g (0.5 mol) of sodium formyl acetic acid methyl ester (content 85 wt.-%) is reacted as in Example 1, but with the addition of 20 g of sodium hydroxide in 80 ml of water. After one hour of reaction at 30° C., 40 g of sodium hydroxide in 50 ml of water and 170 g (1.5 mol) of hydrogen peroxide in the form of a 30 wt.-% solution are added over a period of one-half hour; the mixture is maintained at 60° C. and cooled to 20° C. The addition of hydrochloric acid is performed as in Example 1.

Yield: 44.9 g (80.1% of the theory).

It will be understood that the specification and examples are illustrative but not limitative of the present invention and that other embodiments within the spirit and scope of the invention will suggest themselves to those skilled in the art.

We claim:

1. A method of preparing uracil

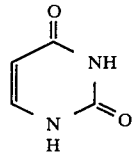

(1)

comprising reacting an alkali formyl acetic alkyl ester

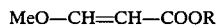

MeO—CH=CH—COOR (2)

wherein Me represents an alkali metal, preferably sodium or potassium, and R represents an alkyl moiety of 1 to 8 carbon atoms, with thiourea to form an alkali salt of 2-mercapto-4-hydroxypyrimidine

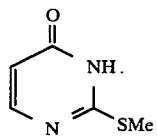

(3)

wherein Me has the same meaning as in Formula 2; reacting without isolation, the alkali salt with hydrogen peroxide in aqueous solution, in the presence of at least 2 moles of base, and acidifying to a pH of 6 or less.

2. The method of claim 1, wherein the molar ratio of hydrogen peroxide to thiourea is 2 to 8, and is preferably 2.5 to 5 to 1.

3. The method of claim 2, wherein the reaction is performed with hydrogen peroxide at 0° to 150° C., and preferably at 10° to 100° C.

4. The method of claim 2, wherein the reaction with hydrogen peroxide, the molar ratio of total base to thiourea amounts to 2.5 to 8 to 1, and is preferably 3.5 to 5 to 1.

5. The method of claim 1, wherein the uracil, after the reaction with hydrogen peroxide, is released by acidification to a pH of preferably 3 or less.

6. The method of claim 1, wherein R is a methyl or ethyl moiety.

7. The method of claim 6, wherein the molar ratio of hydrogen peroxide to thiourea is 2 to 8, and is preferably 2.5 to 5 to 1.

8. The method of claim 7, wherein the reaction is performed with hydrogen peroxide at 0° to 150° C., and preferably at 10° to 100° C.

9. The method of claim 7, wherein the reaction with hydrogen peroxide, the molar ratio of total base to thiourea amounts to 2.5 to 8 to 1, and is preferably 3.5 to 5 to 1.

10. The method of claim 6, wherein the uracil, after the reaction with hydrogen peroxide, is released by acidification to a pH of preferably 3 or less.

* * * * *